United States Patent
Oka

(10) Patent No.: US 9,534,810 B2
(45) Date of Patent: *Jan. 3, 2017

(54) HEATING ELEMENT AND HEATING IMPLEMENT

(71) Applicant: KAO CORPORATION, Chuo-ku (JP)

(72) Inventor: Takeshi Oka, Funabashi (JP)

(73) Assignee: KAO CORPORATION, Chuo-ku (JP)

( * ) Notice: Subject to any disclaimer, the term of this patent is extended or adjusted under 35 U.S.C. 154(b) by 301 days.

This patent is subject to a terminal disclaimer.

(21) Appl. No.: 14/364,165

(22) PCT Filed: Dec. 21, 2012

(86) PCT No.: PCT/JP2012/083304
§ 371 (c)(1),
(2) Date: Jun. 10, 2014

(87) PCT Pub. No.: WO2013/094745
PCT Pub. Date: Jun. 27, 2013

(65) Prior Publication Data
US 2014/0373828 A1    Dec. 25, 2014

(30) Foreign Application Priority Data

Dec. 21, 2011  (JP) ................ 2011-280534

(51) Int. Cl.
*A61F 7/03*    (2006.01)
*F24J 1/00*    (2006.01)
(Continued)

(52) U.S. Cl.
CPC ............... *F24J 1/00* (2013.01); *A61F 7/034* (2013.01); *A61F 2007/0062* (2013.01);
(Continued)

(58) Field of Classification Search
CPC ............... F24J 1/00; A61F 7/034; A61F 7/03; A61F 7/00; A61F 7/02; A61F 2007/0062
(Continued)

(56) References Cited

U.S. PATENT DOCUMENTS

| | | |
|---|---|---|
| 3,976,049 A | 8/1976 | Yamashita et al. |
| 6,436,128 B1 | 8/2002 | Usui |

(Continued)

FOREIGN PATENT DOCUMENTS

| | | |
|---|---|---|
| CN | 101330887 A | 12/2008 |
| EP | 1 147 752 A1 | 10/2001 |

(Continued)

OTHER PUBLICATIONS

U.S. Appl. No. 14/405,943, filed Dec. 5, 2014, Oka, et al.
(Continued)

*Primary Examiner* — Gregory Huson
*Assistant Examiner* — Nikhil Mashruwala
(74) *Attorney, Agent, or Firm* — Oblon, McClelland, Maier & Neustadt, L.L.P.

(57) ABSTRACT

A heating element (10) comprises an exothermic layer (11) containing an oxidizable metal, a water absorption agent and water and a water-retention layer (12) having a water absorption sheet (102), the exothermic layer (11) and the water-retention layer (12) are in layers, in which the mass ratio of the content of the water absorption agent is from 0.3 to 20 parts by mass for 100 parts by mass of the oxidizable metal, mass ratio of content of water to the content of the water absorption agent in the exothermic layer (11) (water/water absorption agent) is from 0.8 to 13, and the content of water contained in the water-retention layer (12) is from 10 to 45 mass % of the maximum water absorption of said water-retention layer (12).

16 Claims, 6 Drawing Sheets

(51) Int. Cl.
*A61F 7/00* (2006.01)
*A61F 7/02* (2006.01)

(52) U.S. Cl.
CPC . *A61F 2007/0098* (2013.01); *A61F 2007/026* (2013.01); *A61F 2007/0214* (2013.01); *A61F 2007/0258* (2013.01)

(58) Field of Classification Search
USPC ........ 126/263.05, 263.01, 204, 206; 122/21; 53/396, 431; 607/96, 114
See application file for complete search history.

(56) References Cited

U.S. PATENT DOCUMENTS

| | | | |
|---|---|---|---|
| 6,863,682 | B2 | 3/2005 | Usui |
| 7,537,002 | B2 * | 5/2009 | Handa ............... A47J 36/28 126/263.01 |
| 7,611,767 | B2 | 11/2009 | Usui et al. |
| 8,137,392 | B2 | 3/2012 | Friedensohn et al. |
| 8,256,412 | B2 * | 9/2012 | Kumamoto ........... A61F 7/034 126/204 |
| 9,389,503 | B2 * | 7/2016 | Tokunaga ............. G03C 1/047 |
| 2002/0151947 | A1 | 10/2002 | Usui |
| 2004/0042965 | A1 | 3/2004 | Usui et al. |
| 2004/0112366 | A1 | 6/2004 | Addison et al. |
| 2004/0149732 | A1 | 8/2004 | Usui et al. |
| 2006/0154006 | A1 | 7/2006 | Usui et al. |
| 2007/0142882 | A1 | 6/2007 | Quincy, III et al. |
| 2007/0156213 | A1 | 7/2007 | Friedensohn et al. |
| 2009/0101867 | A1 | 4/2009 | Ishikawa et al. |
| 2009/0149925 | A1 | 6/2009 | MacDonald et al. |
| 2009/0320411 | A1 * | 12/2009 | Carvallo ............. B65B 29/10 53/433 |
| 2010/0198325 | A1 | 8/2010 | Ishikawa |
| 2010/0241199 | A1 | 9/2010 | Hidaka et al. |
| 2011/0073099 | A1 * | 3/2011 | Madan ................. A47J 36/28 126/263.02 |
| 2013/0125837 | A1 | 5/2013 | Ueno et al. |
| 2016/0128866 | A1 * | 5/2016 | Oka ..................... A61F 7/034 126/204 |

FOREIGN PATENT DOCUMENTS

| | | |
|---|---|---|
| EP | 1 923 447 A1 | 5/2008 |
| EP | 2 177 183 A1 | 4/2010 |
| JP | 9-75388 | 3/1997 |
| JP | 2002-155273 A | 5/2002 |
| JP | 2003-129041 | 5/2003 |
| JP | 2004-26904 | 1/2004 |
| JP | 2004-208978 | 7/2004 |
| JP | 2007-319359 A | 12/2007 |
| TW | 200403048 A | 3/2004 |
| WO | WO 2007/075277 A1 | 7/2007 |
| WO | WO 2011/158919 A1 | 12/2011 |

OTHER PUBLICATIONS

Extended European Search Report issued Jul. 9, 2015 in Patent Application No. 12860770.2.
Singaporean Search Report issued Sep. 21, 2015 in Patent Application No. 10201506236P.
Combined Taiwanese Office Action and Search Report issued Jan. 28, 2016 in Patent Application No. 104126277 (with English translation of categories of cited documents).
Combined Taiwanese Office Action and Search Report issued Dec. 25, 2014 in Patent Application No. TW101149222 (with English Translation of Category of Cited Documents).
International Search Report issued Jan. 29, 2013, in PCT/JP12/083304 filed Dec. 21, 2012.

\* cited by examiner

FIG.6
(a)
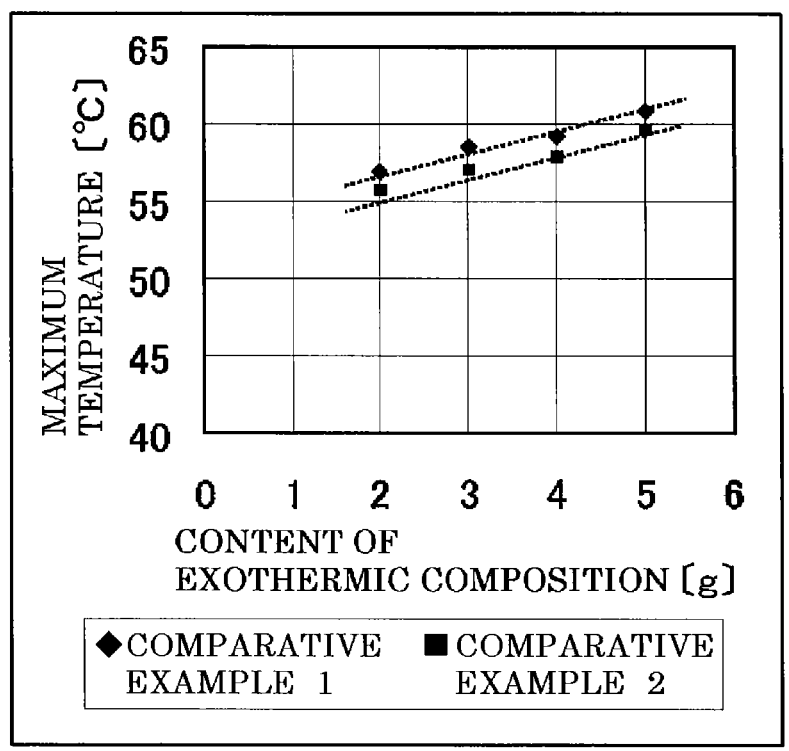
(b)
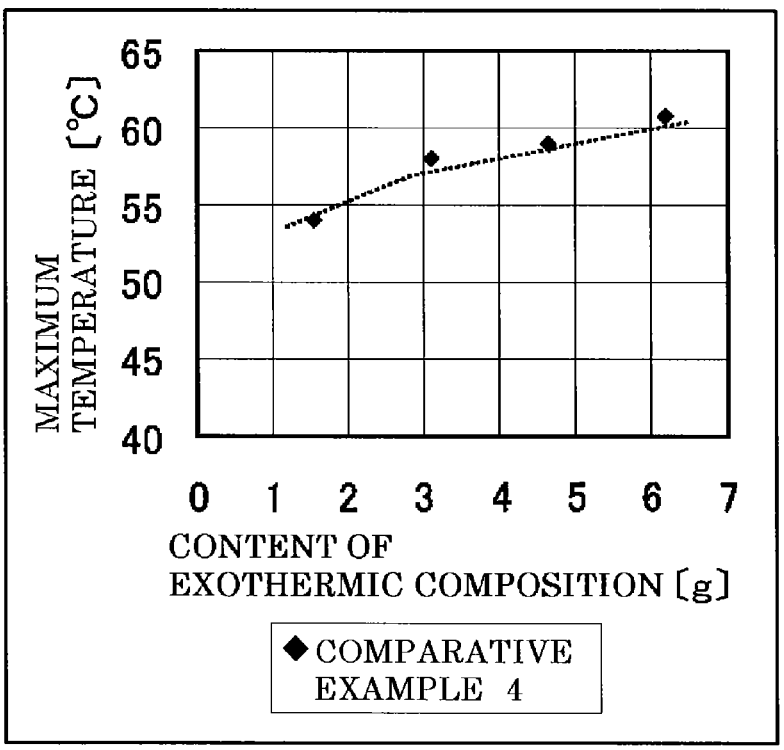

HEATING ELEMENT AND HEATING IMPLEMENT

TECHNICAL FIELD

The present invention relates to a heating element and a heating implement including the heating element.

BACKGROUND OF THE INVENTION

Exothermic compositions constituting oxidizable metals, such as iron powder and the like, carbon components, and water, which produce heat by an oxidation reaction of an oxidizable metal, are known as, for example, those described in Patent Documents 1 and 2.

Patent Document 1 describes an ink-like or cream-like exothermic composition. It is described therein that the use of this exothermic composition prevents the generation of dust during the production of the heating element and suppresses the exothermic reaction of the exothermic composition, so that loss due to the exothermic reaction during the production, deterioration in the quality of the exothermic composition and/or solidification can be prevented.

Patent Document 2 describes an exothermic composition, having enhanced formability and shape retention ability and also having exothermic characteristics by establishing the particle diameter of the solid component of the exothermic composition and the excessive water within appropriate ranges, in which a heat-generating reaction can be started by coming in contact with air immediately after forming, and a heating element employing the same.

RELATED DOCUMENTS

Patent Documents

[Patent Document 1]
Japanese Laid-Open Patent Publication No. 1997-75388
[Patent Document 2]
Japanese Laid-Open Patent Publication No. 2004-208978

SUMMARY OF INVENTION

According to one aspect of the present invention, there is provided a heating element including:
an exothermic layer containing an oxidizable metal, a water absorption agent and water; and
a water-retention layer having a water absorption sheet, wherein the exothermic layer and the water-retention layer are in layers, wherein the mass ratio of the content of the water absorption agent is from 0.3 to 20 parts by mass for 100 parts by mass of the oxidizable metal,
wherein the mass ratio of the content of water to the content of the water absorption agent in the exothermic layer (water/water absorption agent) is from 0.8 to 13, and
wherein the content of water in the water-retention layer is from 10 to 45 mass % of the maximum water absorption of the water-retention layer; further, there is also provided a heating implement containing the heating element.

BRIEF DESCRIPTION OF THE DRAWINGS

The advantages and features of the present invention will be more apparent from the following description of certain preferred embodiments taken in conjunction with the accompanying drawings.

FIG. 6 contains graphs, which show evaluation results of Comparative Examples.

DESCRIPTION OF EMBODIMENTS

If the exothermic composition is charged with an excessive quantity in a single package, or if a large amount of the exothermic composition is unevenly distributed in a specific section for some reason during the production of the heating element, the generation of heat may be unusually accelerated in such package or in such section of the package, causing trouble of unusual heat generation.

The present inventors have found that even if the exothermic composition is charged with an excessive amount in a single package or a large amount of the exothermic composition is unevenly distributed in a specific section, for some reason in the production of the heating element, a specific quantity of water is contained in the water-retention layer to increase the heat capacity thereof in the layered structure of the water-retention layer and the exothermic layer to prevent the unwanted anomalous heat generation, so that the heating element, which stably exhibits improved exothermic characteristics, can be provided.

In addition to the above, the problem of possibly producing a product which can cause unusual heat generation due to fluctuations in the production conditions during the production process or in the components of the raw materials has not been examined in the conventional technologies.

The heating element of the present embodiment includes:
an exothermic layer containing an oxidizable metal, a water absorption agent and water; and
a water-retention layer having a water absorption sheet, wherein the exothermic layer and the water-retention layer are in layers, wherein the mass ratio of the content of the water absorption agent is from 0.3 to 20 parts by mass for 100 parts by mass of the oxidizable metal,
wherein the mass ratio of the content of water to the content of the water absorption agent in the exothermic layer (water/water absorption agent) is from 0.8 to 13, and
wherein the content of water in the water-retention layer is from 10 to 45 mass % of the maximum water absorption of the water-retention layer.

According to such heating element, even if the exothermic composition is charged with an excessive amount in a single package or a large amount of the exothermic composition is unevenly distributed in a specific section for some reason in the production of the heating element, a specific quantity of water is contained in the water-retention layer to increase the heat capacity thereof in the layered structure of the water-retention layer and the exothermic layer, so that improved exothermic characteristics can be stably obtained.

Exemplary implementations according to the present invention will be described in detail as follows in reference to the annexed figures. In all figures, an identical numeral is assigned to an element commonly appeared in the figures, and the detailed description thereof will not be repeated.

Figure 1:
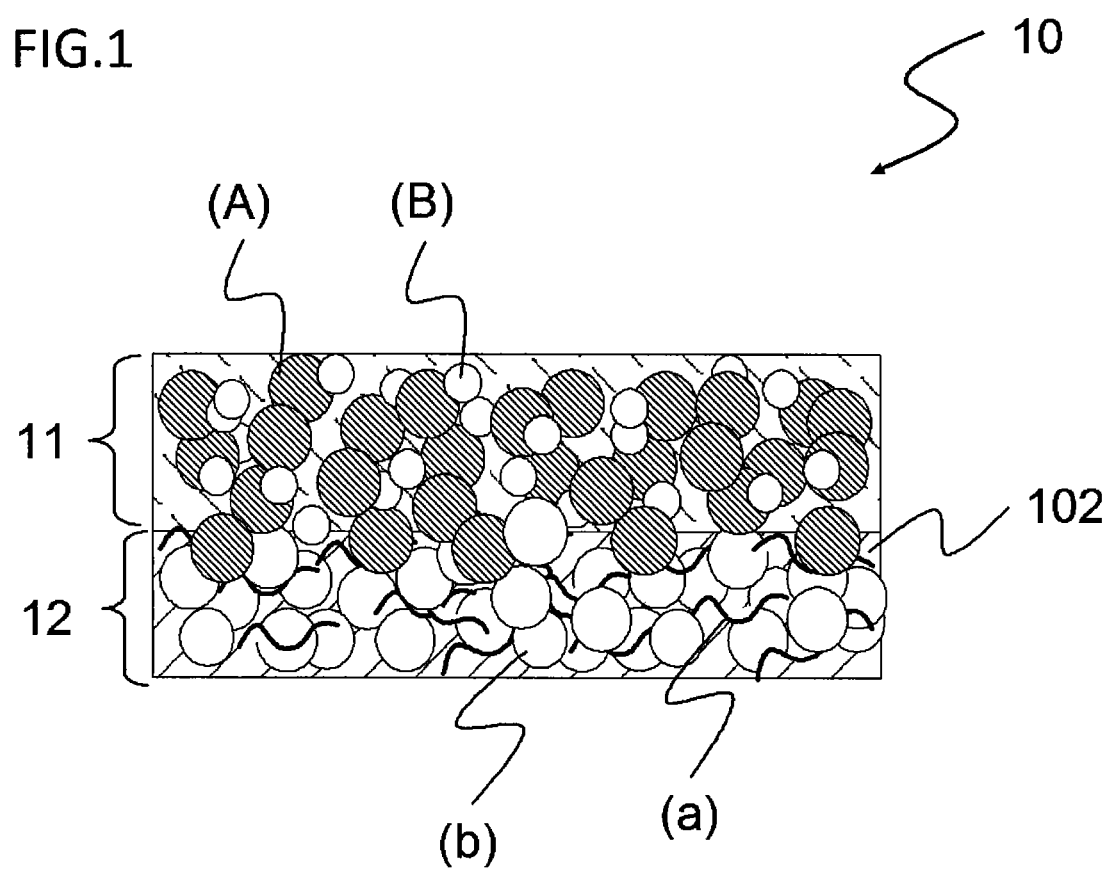
FIG. 1 is a cross-sectional view, which schematically shows a heating element according to an embodiment.

FIG. 1 is a cross-sectional view, which schematically shows a heating element 10 according to the present embodiment. The heating element 10 is composed of an exothermic layer 11, and a water-retention layer 12 that is layered thereon. The exothermic layer 11 contains an oxidizable metal ((A) in FIG. 1), a water absorption agent ((B) in FIG. 1) and water. The water-retention layer 12 is formed of a water absorption sheet 102.

The heating element 10 serves as providing a sufficient heating effect with heat generated by the oxidation reaction of the oxidizable metal, and is capable of exhibiting the performance of the exothermic temperature of from 38 to 70 degrees C. in the measurement based upon Japanese Industrial Standard (JIS) S 4100. The heating element 10 may be a vapor heat generation implement accompanied with the generation of water vapor, or a so-called disposable heating pad, which can produce heat substantially without generation of water vapor.

The oxidizable metal is a metal that is capable of releasing heat by an oxidation reaction, and typically includes, for example, powder or fiber, of one, two or more selected from iron, aluminum, zinc, manganese, magnesium, and calcium. Among these, iron powder is preferable in view of handleability, safety, manufacturing cost, storage stability and stability. Typical iron powder includes, for example, one, two or more selected from reduced iron powder and atomized iron powder.

When the oxidizable metal is powder, the mean particle diameter of the powder is preferably from 10 to 200 μm in terms of the fact that the oxidation reaction is effectively conducted, and the mean particle diameter is more preferably from 20 to 150 μm. Here, the particle diameter of the oxidizable metal means the maximum length in the conformation of the powder, and can be determined by the classification with sieves, dynamic light scattering, laser diffractometry or the like.

In view of the similar aspect, the mean particle diameter of the oxidizable metal is equal to or larger than 10 μm, and is further preferably equal to or larger than 20 μm. On the other hand, the mean particle diameter is equal to or smaller than 200 μm, and is preferably equal to or smaller than 150 μm.

The content of oxidizable metal is preferably from 100 to 3,000 $g/m^2$ represented with the grammage, and is further preferably from 200 to 1,500 $g/m^2$. This allows increasing the exothermic temperature of the heating element 10 to a desired temperature. Here, the content of the iron powder in the heating element 10 can be determined by an ash test pursuant to JIS P 8128, or by employing a thermogravimetry device. Another measurement may utilize a property of causing magnetization by applying an external magnetic field to carry out the quantification via the vibrating sample magnetometer test or the like.

In view of the similar aspect, the content of the oxidizable metal is preferably equal to or higher than 100 $g/m^2$ represented by the grammage, and is more preferably equal to or higher than 200 $g/m^2$. On the other hand, the content of the oxidizable metal is preferably equal to or lower than 3,000 $g/m^2$, and is more preferably equal to or lower than 1,500 $g/m^2$.

The water absorption agent is a material having water-retention ability, and typically is, for example, one, two or more selected from carbon components, fiber materials, water-absorbing polymers and water-absorbing powder.

The carbon component possesses water-retention ability, oxygen supply ability and catalytic ability, and typically, for example, one, two or more selected from activated carbon, acetylene black, and black-lead may be available, and among these, activated carbon is preferably employed, in view of easy adsorption of oxygen in the wetted condition, in view of constant retention of water of the exothermic layer, and in view of easy establishment of the content of the water contained in water-retention layer 12 as being from 10 to 45 mass % of the maximum water absorption of the water-retention layer 12. More preferably, one, two or more of fine powdered material(s) or granular material(s) selected from coconut shell carbon, wood powder carbon and peat may be employed. Among these, the wood powder carbon is preferable, since the use thereof allows constantly maintaining the moisture level in the exothermic layer 11 to maintain the content of the water contained in the water-retention layer 12 as being from 10 to 45 mass % of the maximum water absorption of the water-retention layer 12.

It is preferable to employ the carbon component having the mean particle diameter of from 10 to 200 μm, not only from the standpoint of achieving the uniform mixing with the oxidizable metal but also from the standpoint of maintaining the content of the water contained in the water-retention layer 12 as being from 10 to 45 mass % of the maximum water absorption of the water-retention layer 12, and it is more preferable to employ that having the mean particle diameter of from 12 to 100 μm. Here, the particle diameter of the carbon component means the maximum length in the conformation of the powder, and can be determined by the dynamic light scattering, the laser diffractometry or the like. While the carbon component having the form of the powder is preferably employed, those having the form other than the powder may alternatively be employed, and for example, those having the fibrous form may be employed.

In view of the similar aspect, the mean particle diameter of the carbon component is equal to or larger than 10 μm, and is further preferably equal to or larger than 12 μm. On the other hand, the mean particle diameter of the carbon component is equal to or smaller than 200 μm, and is further preferably equal to or smaller than 100 μm.

Preferable fiber materials may include hydrophilic fibers, and among these, cellulose fibers may be more preferably employed. Typical cellulose fibers available here may include chemical fibers (synthetic fibers) and natural fibers.

Typical water-absorbing polymers may include a hydrophilic polymer having the cross-link structure that is capable of absorbing and maintaining a significant amount of liquid that is 20 times of their own weight.

Typical water-absorbing powders may include one, two or more selected from vermiculite, sawdust, silica gel and pulp powder.

The content of the water absorption agent is from 0.3 to 20 parts by mass for 100 parts by mass of the oxidizable metal, and is more preferably from 1 to 15 parts by mass, and is further preferably from 3 to 13 parts by mass. This allows accumulating an amount of water required for sustaining the oxidation reaction in the obtained heating element 10. Another advantage is that a sufficient level of the oxygen supply to the heating element 10 can be achieved to obtain the heating element exhibiting enhanced exothermic efficiency. In addition, the heat capacity of the heating element 10 for the acquired amount of the heat generation can be reduced, so that the temperature elevation due to the heat generation is increased to achieve the desired temperature elevation. In the meantime, the content of the water absorption agent represented by the grammage is preferably from 4 to 290 g/m², and is further preferably from 7 to 160 g/m².

In addition to the above, the content of the water absorption agent is preferably equal to or higher than 1 parts by mass for 100 parts by mass of the oxidizable metal, and is further preferably equal to or higher than 3 parts by mass. On the other hand, the content of the water absorption agent is preferably equal to or lower than 15 parts by mass for 100 parts by mass of the oxidizable metal, and is more preferably equal to or lower than 13 parts by mass.

In the meantime, the content of the water absorption agent represented by the grammage is preferably equal to or higher than 4 g/m² and is further preferably equal to or higher than 7 g/m², and on the other hand, is preferably equal to or lower than 290 g/m², and is further preferably equal to or lower than 160 g/m².

It is preferable in terms of suitably controlling the water content in the exothermic layer 11 that the content of the carbon component in the water absorption agent is equal to or higher than 90 mass % for the whole mass of the water absorption agent, and more preferably equal to or higher than 95 mass %, and further preferably equal to or higher than 98 mass %, and it is still further preferable that the water absorption agent is composed only of the carbon component.

Further, the content of the water-absorbing polymer in the water absorption agent is equal to or lower than 10 mass % for the whole quantity of the water absorption agent, is preferably equal to or lower than 5 mass % and is further preferably equal to or lower than 2 mass %, and it is still further preferable to contain none of the water-absorbing polymer in the exothermic layer 11, since this constitution reduces the heat capacity of the heating element for the acquired amount of the heat generation to provide increased temperature elevation by the heat generation, thereby providing the desired temperature elevation.

Mass ratio of the content of water to the content of the water absorption agent (water/water absorption agent) in the exothermic layer 11 is from 0.8 to 13, preferably from 1 to 12, and more preferably from 1.5 to 10. This can more desirably maintain the content of water contained in the water-retention layer 12 to be from 10 to 45 mass % of the maximum water absorption of the water-retention layer 12. Further, this also ensures sufficient air permeability through the heating element 10 to provide sufficient oxygen supply, thereby providing the heating element exhibiting enhanced exothermic efficiency. This constitution also reduces the heat capacity of the heating element for the acquired amount of the heat generation to provide increased temperature elevation by the heat generation, thereby providing the desired temperature elevation.

In addition, the mass ratio of the content of water to the content of the water absorption agent (water/water absorption agent) is preferably equal to or higher than 1, and is further preferably equal to or higher than 1.5. On the other hand, the mass ratio of the content of water to the content of the water absorption agent (water/water absorption agent) is preferably equal to or lower than 12, and is further preferably equal to or lower than 10.

The heating element 10 of the present invention includes the exothermic layer 11 and the water-retention layer 12, both of which are stacked, and the water-retention layer 12 is formed of the water absorption sheet 102. The content of water contained in the water-retention layer 12 is from 10 to 45 mass % of the maximum water absorption of the water-retention layer 12, and is preferably from 12 to 40 mass %, and it is more preferable to be from 13 to 30 mass %, since unusual heat generation is prevented so that improved exothermic characteristics can be stably obtained, even if the exothermic composition is charged with an excessive amount in a single package or a large amount of the exothermic composition is unevenly distributed in a specific section for some reason in the production of the heating element. Further, the maximum water absorption is determined by a method described in Examples as will be discussed later.

In view of the similar aspect, the content of water contained in the water-retention layer 12 is equal to or higher than 12 mass % of the maximum water absorption of the water-retention layer 12, and is preferably equal to or higher than 13 mass %.

On the other hand, the content of water contained in the water-retention layer 12 is equal to or lower than 40 mass % thereof, and is more preferably equal to or lower than 30 mass %.

The water-retention layer 12 is only necessary to have the water absorbability for absorbing and maintaining water of from 10 to 45 mass % of the maximum water absorption. The water-retention layer 12 preferably has air permeability, although air permeability may or may not be provided.

Air resistance of the water-retention layer 12 under the condition that water of from 10 to 45 mass % of the maximum water absorption is absorbed, is preferably equal to or lower than 500 seconds/100 ml, and is more preferably from 1 to 300 seconds/100 ml. Such air resistance ensures sufficient air permeability through the heating element 10 to provide sufficient oxygen supply to provide the heating element exhibiting enhanced exothermic efficiency, such that improved oxidation reaction of the oxidizable metal can be achieved and a large quantity of water vapor can be generated. In the present specification, air resistance is a value measured according to JIS P 8117, and is defined as the time required for air of 100 ml to pass through an area of 6.45 cm² under constant pressure. Air resistance can be measured with an Oken type air-permeability tester or similar tester. The air resistance is preferably equal to or lower than 300 seconds/100 ml. On the other hand, in view of preventing excessive temperature elevation, it is preferably equal to or higher than 1 second/100 ml.

The water-retention layer 12 may be composed of a sheet containing the component (a): fiber material of, for example, a single ply of a fiber sheet, or may alternatively be composed of two or more stacked plies thereof. The fiber sheet specifically includes papers or nonwoven fabrics produced of fiber materials as will be discussed later, or products composed of stacked papers and nonwoven fabrics. The sheet containing the component (a): fiber material, may be more specifically a sheet material composed of a paper or a nonwoven fabric that is formed of a material without water absorbability such as polyethylene fiber, polypropylene fiber, polyethylene sheet, polypropylene sheet and the like, on which a fiber material is layered or laminated, or a sheet material composed of paper-produced or nonwoven fabric that is formed of a fiber material such as a pulp fiber or a rayon fiber and another fiber material, which is layered thereon or mixed therein. The use of the sheet containing the component (a): fiber material in the water-retention layer 12 is preferable since it allows easy establishment of the content of water contained in the water-retention layer 12 to be from 10 to 45 mass % of the maximum water absorption of the water-retention layer 12.

The water-retention layer 12 may further contain the component (b): water-absorbing polymer. FIG. 1 illustrates an example, in which the water-retention layer 12 includes the component (a): fiber material, and, the component (b): water-absorbing polymer. When the water-retention layer 12 contains the component (b), the illustrated conformation of the water-retention layer 12 may include:
(i) the component (a) and the component (b) uniformly mixed to form a single sheet;
(ii) the component (b) disposed between same or different sheets containing the component (a); or
(iii) the component (b) sprayed to form the sheet-like material. Among these, the preferable selection may be the conformation of (ii), since this allows easy control of the water content of the exothermic layer 11 to facilitate the adjustment of the content of water contained in the water-retention layer 12 as being from 10 to 45 mass % of the maximum water absorption of the water-retention layer 12. Meanwhile, the water-retention layer 12 of the conformation of (ii) may be produced by, for example, a method, in which the component (b): water-absorbing polymer is uniformly sprayed over a sheet containing the component (a), and 200 g/m$^2$ of water is sprayed thereon, and then the same or different type of a sheet containing the component (a) is further layered thereon and a compression drying is carried out at 100+/−0.5 degrees C. and a pressure of 5 kg/cm$^2$ until the water content is reduced to equal to or lower than 5 mass %.

While any one of a hydrophilic fiber and a hydrophobic fiber may be employed as the component (a): fiber material, it is preferable to employ the hydrophilic fiber, and the cellulose fiber is more preferably employed to promote the transfer of moisture to the water-retention layer 12, thereby allowing easy establishment of the content of water contained in the water-retention layer 12 to be from 10 to 45 mass % of the maximum water absorption of the water-retention layer 12. Typical cellulose fibers that can be used here may include chemical fibers (synthetic fibers) and natural fibers.

As chemical fibers included in the cellulose fibers, for example, rayon and acetate fibers can be used. On the other hand, natural fibers included in the cellulose fibers, for example, one, two or more selected from various types of vegetable fibers, wood pulp fibers, non-wood pulp fibers, cotton fibers, linen fibers, straw fibers, hemp fibers, jute fibers, kapok fibers, palm fibers, and rush grass fibers can be used. Among these cellulose fibers, the wood pulp fibers may be preferably employed to allow easy establishment of the content of water contained in the water-retention layer 12 to be from 10 to 45 mass % of the maximum water absorption of the water-retention layer 12.

Various types of fiber materials may preferably have a fiber length of from 0.5 to 6 mm, and more preferably of from 0.8 to 4 mm. Among these, the fiber material may preferably have a fiber length of equal to or longer than 0.5 mm, and more preferably of equal to or longer than 0.8 mm. On the other hand, the fiber material may preferably have the fiber length of equal to or shorter than 6 mm, and more preferably of equal to or shorter than 4 mm.

In addition to the hydrophilic fiber, a hydrophobic fiber, such as a thermally bonded fiber may be blended in the water-retention layer 12, as required. The blending quantity of the thermally bonded fiber may be preferably from 0.1 to 10 mass % over the whole quantity of the fibers contained in the water-retention layer 12, and may further be preferably from 0.5 to 5 mass %.

In view of the similar aspect, the blending quantity of the thermally bonded fiber may be preferably equal to or larger than 0.1 mass % over the whole quantity of the fibers contained in the water-retention layer 12, and may be preferably equal to or larger than 0.5 mass %. On the other hand, the blending quantity of the thermally bonded fiber may be preferably equal to or smaller than 10 mass % over the whole quantity of the fibers contained in the water-retention layer 12, and may be preferably equal to or smaller than 5 mass %.

The hydrophilic polymer having the cross-link structure, which is capable of absorbing and maintaining a significant amount of liquid that is 20 times its own weight, is employed as the component (b): water-absorbing polymer, similarly as the above-described fiber materials, such that the content of water contained in the water-retention layer 12 may be preferably maintained to be from 10 to 45 mass % of the maximum water absorption of the water-retention layer 12. The shape of the component (b) may be one, two or more selected from spherical form, massive form, grape cluster form and fibrous form. The particle diameter of the component (b) is preferably from 1 to 1,000 μm, and is further preferably from 10 to 500 μm. In addition to the above, the particle diameter of the water-absorbing polymer particles may be determined by the dynamic light scattering, the laser diffractometry or the like. The particle diameter of the component (b) is preferably equal to or larger than 1 μm, and is further preferably equal to or larger than 10 μm.

On the other hand, the particle diameter of the component (b) is preferably equal to or smaller than 1,000 μm, and is further preferably equal to or smaller than 500 μm.

Specific examples of the component (b) includes, for example, one, two or more selected from polyacrylic acids and their salts and polyacrylate graft polymers, such as starch, cross-linked carboxymethyl cellulose, polymers or copolymers of acrylic acids or alkali metal salts of acrylic acids and the like. Among these, polyacrylic acids and their salts and polyacrylate graft polymers such as polymers or copolymers of acrylic acids or alkali metal salts of acrylic acids and the like is preferably employed to sufficiently maintain the content of water contained in the water-retention layer 12 as being from 10 to 45 mass % of the maximum water absorption of the water-retention layer 12.

Ratio of the component (b) to the water-retention layer 12 is preferably from 10 to 70 mass % under the dried condition, and is further preferably from 20 to 65 mass % to promote rapid transfer of moisture to the water-retention layer 12, thereby suitably maintaining the content of water contained in the water-retention layer 12 as being from 10 to 45 mass % of the maximum water absorption of the water-retention layer 12.

In view of the similar aspect, the ratio of the component (b) to the water-retention layer 12 is preferably equal to or higher than 10 mass % under the dried condition, and is further preferably equal to or higher than 20 mass %, and on the other hand is preferably equal to or lower than 70 mass % under the dried condition, and is more preferably equal to or lower than 65 mass %.

The water-retention layer 12 may preferably have its own grammage of from 20 to 200 g/m$^2$ under the dried condition, in view of achieving easy adjustment of the content of water contained in the water-retention layer 12 as being from 10 to 45 mass % of the maximum water absorption of the water-retention layer 12, and in addition, preferably as being from 35 to 150 g/m$^2$, and further preferably as being from 50 to 140 g/m$^2$. The grammage of the component (b) contained in the water-retention layer 12 is preferably from 5 to 150 g/m$^2$ under the dried condition, in view of suitably maintaining the content of water contained in the water-retention layer 12 as being from 10 to 45 mass % of the maximum water absorption of the water-retention layer 12, and in addition, is preferably from 10 to 100 g/m², and is further preferably from 30 to 90 g/m².

The water-retention layer 12 preferably has the grammage under the dried condition of equal to or larger than 20 g/m², and further is preferably equal to or larger than 35 g/m², and is more preferably equal to or larger than 50 g/m². On the other hand, the water-retention layer 12 preferably has the grammage under the dried condition of equal to or smaller than 200 g/m², and further is preferably equal to or smaller than 150 g/m², and is even more preferably equal to or smaller than 140 g/m².

The grammage of the component (b) contained in the water-retention layer 12 is equal to or larger than 5 g/m² under the dried condition, and further, is preferably equal to or larger than 10 g/m², and is more preferably equal to or larger than 30 g/m². On the other hand, the water-retention layer 12 preferably has the grammage under the dried condition of equal to or smaller than 150 g/m², and further is preferably equal to or smaller than 100 g/m², and is more preferably equal to or smaller than 90 g/m².

Figure 2:
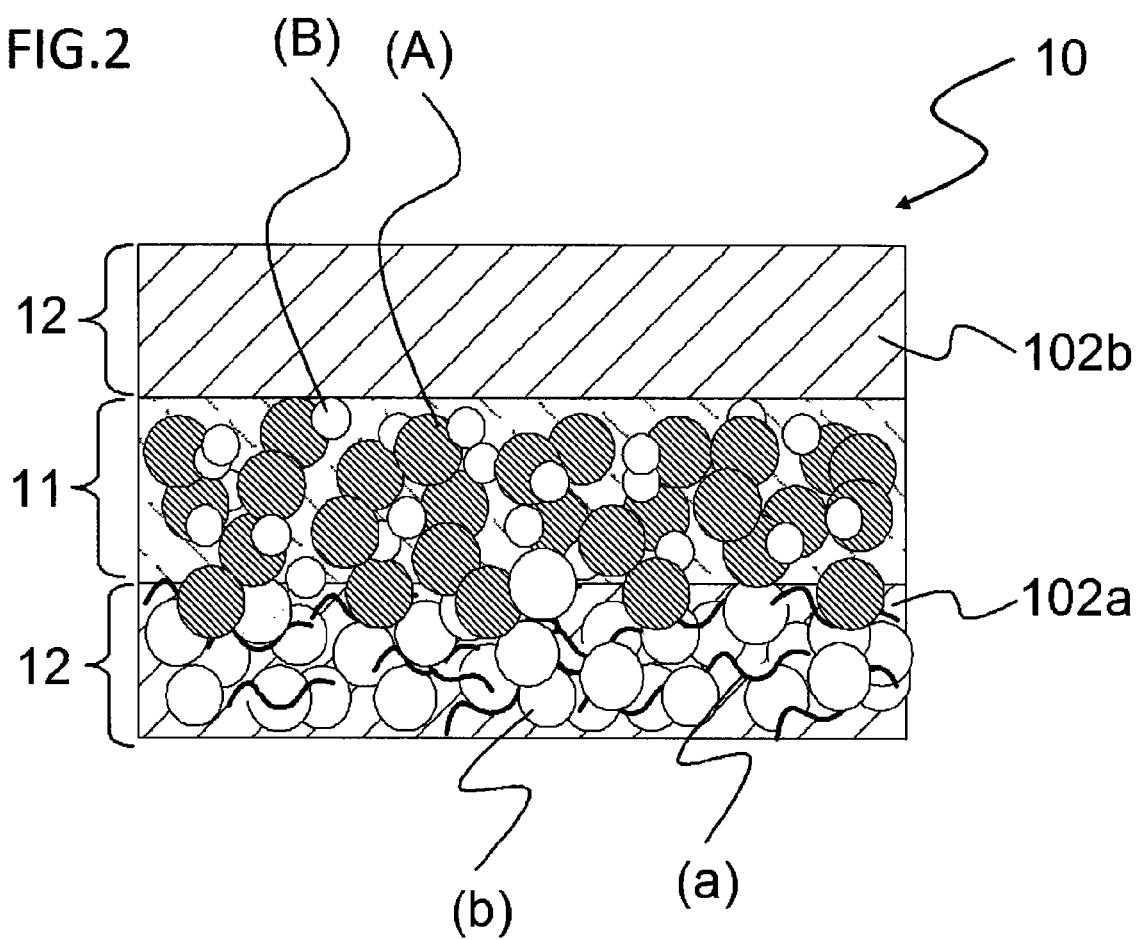
FIG. 2 is a cross-sectional view, which schematically shows a modified embodiment of a heating element according to an embodiment.

The water-retention layer 12 may be constituted to have the exothermic layer 11, which is formed on one side of the water-retention layer 12 as show in FIG. 1, or alternatively be constituted to have the exothermic layers 11, which are formed on both sides of the water-retention layer 12. In addition, as shown in FIG. 2, the water-retention layer 12 may be formed of a first water absorption sheet 102a and a second water absorption sheet 102b. In such case, the heating element 10 may have a structure, in which the exothermic layer 11 is interposed between the first water absorption sheet 102a and the second water absorption sheet 102b, being a so-called sandwich structure. The first water absorption sheet 102a may be composed of a material that is the same as, or that is different from, the material composing the second water absorption sheet 102b. For example, if the first water absorption sheet 102a is composed of a multiple-layered material of two or more of fiber sheets, or of a material containing the component (a): fiber material and the component (b): water-absorbing polymer and the second water absorption sheet 102b is composed of a single fiber sheet, this constitution can provide easy control of the content of water contained in the water-retention layer 12 as being from 10 to 45 mass % of the maximum water absorption of the water-retention layer 12 and can also provide enhanced oxidation reaction of the oxidizable metal, and therefore this constitution is preferable. In such case, it is only necessary that the second water absorption sheet 102b covers at least a portion of the exothermic layer 11, and it is preferable that the second water absorption sheet 102b covers the entire surface of the exothermic layer 11.

In addition, under the condition that the content of water contained in the water-retention layer 12 is from 10 to 45 mass %, both of the first water absorption sheet 102a and the second water absorption sheet 102b may preferably have the air resistance of equal to or lower than 500 seconds/100 ml. In addition to the above, the lower limit thereof is, for example, 1 second/100 ml.

The heating element 10 may further contain a reaction accelerator agent. The reaction accelerator agent is employed for the purpose of sustaining the oxidation reaction of the oxidizable metal.

In addition, the use of the reaction accelerator agent can break an oxide film, which has been created in the oxidizable metal due to the oxidation reaction, to accelerate the oxidation reaction. Typical reaction accelerator agent includes, for example, one, two or more selected from sulfates and chlorides of alkali metals and alkaline earth metals. Among these, in view of providing enhanced electroconductivity and chemical stability, and reduced production costs, it is preferable to employ one, two or more selected from various types of chlorides such as sodium chloride, potassium chloride, calcium chloride, magnesium chloride, ferrous chloride, ferric chloride and the like; and sodium sulfate.

The content of the reaction accelerator agent in the heating element 10 is preferably from 2 to 15 parts by mass for 100 parts by mass of the oxidizable metal, in view of sustaining sufficient amount of heat generation for longer time duration, and is further preferably from 3 to 13 parts by mass. In view of the similar aspect, the content of the reaction accelerator agent in the heating element 10 is preferably equal to or larger than 2 parts by mass for 100 parts by mass of the oxidizable metal, and is further preferably equal to or larger than 3 parts by mass. On the other hand, the content of the reaction accelerator agent in the heating element 10 is equal to or smaller than 15 parts by mass for 100 parts by mass of the oxidizable metal, and is further preferably equal to or smaller than 13 parts by mass.

The heating element 10 may further contain a thickening agent. Substances, which is capable of absorbing water to increase consistency or is capable of providing thixotropic property, may be mainly employed for the thickening agent, and a single substance selected from, or a mixture of two or more selected from: alginates such as sodium alginate and the like; polysaccharide-based thickening agents such as arabian gum, tragacanth gum, locust bean gum, guar gum, arabia gum, carrageenan, agar, xanthan gum and the like; starch-based thickening agents such as dextrin, pregelatinized starch, starch for processing and the like; cellulose derivative-based thickening agents such as carboxymethyl cellulose, ethyl acetate cellulose, hydroxyethyl cellulose, hydroxymethyl cellulose, hydroxypropyl cellulose and the like; metallic soap-based thickening agents such as stearate and the like; mineral-based thickening agents such as bentonite and the like. Among these, in view of providing enhanced coating performance and maintaining the content of water contained in the water-retention layer 12 as being from 10 to 45 mass % of the maximum water absorption of the water-retention layer 12, the polysaccharide-based thickening agent is preferable, and further, the polysaccharide-based thickening agent having the molecular weight of equal to or higher than 1,000,000 and equal to or lower than 50,000,000 is preferable, and the polysaccharide-based thickening agent having the molecular weight of equal to or higher than 2,000,000 and equal to or lower than 40,000,000 is more preferable, and in addition, in view of providing improved coating performance and salt resistance, xanthan gum is preferable.

The content of the thickening agent in the heating element 10 is preferably from 0.05 to 5 parts by mass for 100 parts by mass of the oxidizable metal, and further preferably from 0.1 to 4 parts by mass. The content within this range allows the solid contents such as the oxidizable metal, the water absorption agent and the like to be stably dispersed. In addition, this can also provide a thixotropic property to achieve further improved coating performance. This allows to further easily maintain the content of water contained in the water-retention layer 12 as being from 10 to 45 mass % of the maximum water absorption of the water-retention layer 12, and is thus preferable.

In view of the similar aspect, the content of the thickening agent is preferably equal to or larger than 0.05 parts by mass for 100 parts by mass of the oxidizable metal, and is preferably equal to or larger than 0.1 parts by mass. On the other hand, the content of the thickening agent is preferably equal to or smaller than 5 parts by mass for 100 parts by mass of the oxidizable metal, and is more preferably equal to or smaller than 4 parts by mass.

The heating element 10 may additionally contain, as necessary, a surfactant, a drug, a flocculating agent, a coloring agent, a paper strengthening agent, a thickening agent, a pH adjuster, a bulking agent and the like.

Subsequently, an example of a method for producing the heating element 10 will be described. The heating element 10 can be produced by applying, for example, an exothermic powder-water dispersion containing an oxidizable metal, a water absorption agent and water over the water absorption sheet 102 (the water absorption sheet 102*a* if the heating element 10 of FIG. 2 is produced). While the production of the exothermic powder-water dispersion is carried out by mixing all the above-described components at one time, an alternative way may be that the reaction accelerator agent is dissolved in a mixture that has been preliminarily produced by dissolving the thickening agent in water to prepare an aqueous solution, and then, a pre-mixture of the oxidizable metal and the water absorption agent is added therein.

While the mixing of the reaction accelerator agent may be conducted simultaneously with the mixing of other components in the exothermic powder-water dispersion, an alternative way may be that the exothermic powder-water dispersion is applied, and then a solution of the reaction accelerator agent dissolved in water is added thereto via penetration, atomization or dripping and the like, or another alternative way may be to spray the powder of the reaction accelerator agent.

When the above-described exothermic powder-water dispersion is applied over at least one surface of the water absorption sheet 102 (the water absorption sheet 102*a* if the heating element 10 of FIG. 2 is produced), at least a portion of water in the exothermic powder-water dispersion is absorbed by the water absorption sheet 102 to form the exothermic layer 11 on the water absorption sheet 102 (the water absorption sheet 102*a* if the heating element 10 of FIG. 2 is produced). More specifically, the exothermic layer 11 is composed of residual components that have not been absorbed by the water-retention sheet 102 (the water absorption sheets 102*a* and 102*b* if the heating element 10 of FIG. 2 is produced). The exothermic layer 11 may be present on the water-retention layer 12, or alternatively, a lower section of the exothermic layer 11 may be leastwise partly buried in the water-retention layer 102 as shown in FIG. 1. In addition, the exothermic layer 11 may be provided on one surface of the water-retention layer 12, or may be provided on both sides thereof. An example of providing the exothermic layer 11 on one side of the water-retention layer 12 is shown in FIG. 1.

Figure 3:
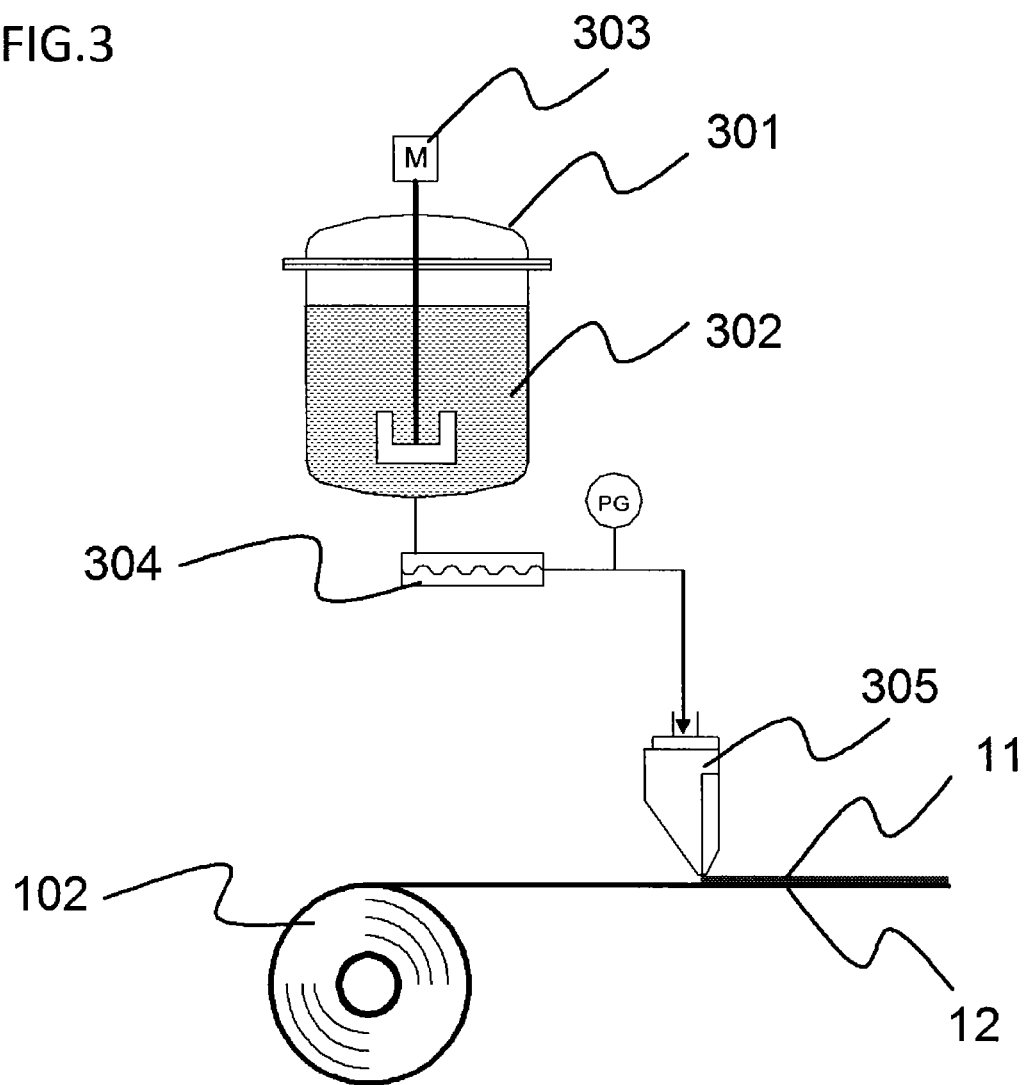
FIG. 3 is a diagram, which is helpful for describing a method for producing a heating element according to an embodiment.

FIG. 3 is a diagram, which is helpful for more specifically describing this production method. First of all, an exothermic powder-water dispersion 302 containing an oxidizable metal, a water absorption agent and water is prepared in a coating vessel 301. The exothermic powder-water dispersion 302 may be stirred by a stirrer 303 to more uniformly disperse the components that are insoluble in water, which typically includes the oxidizable metals, and the water absorption agents and the like. While the production of the exothermic powder-water dispersion 302 is carried out by mixing all the above-described components at one time, an alternative way may be that the reaction accelerator agent is dissolved in a mixture that has been preliminarily produced by dissolving the thickening agent in water to prepare an aqueous solution, and then, a pre-mixture of the oxidizable metal and the water absorption agent is added therein.

Then, the exothermic powder-water dispersion 302 is pumped to a die head 305 by a pump 304. The pumped exothermic powder-water dispersion 302 is pressurized and pushed by employing the die head 305 to be applied over the water absorption sheet 102. At this time, the coating grammage of the exothermic powder-water dispersion 302 is preferably from 160 to 4,800 $g/m^2$, and is more preferably from 320 to 2,200 $g/m^2$.

While FIG. 3 illustrates the coating process via the die coating, the coating method is not limited thereto, and for example, roll coating, screen printing, roll gravure, knife cording, curtain coater and the like may be applicable.

After the coating with the exothermic powder-water dispersion 302, suction may be conducted from the surface where none of the exothermic layer 11 of the heating element 10 is formed. This preferably allows providing enhanced integrity of the water-retention layer 12 and the exothermic layer 11. At this time, suction pressure during the suctioning is preferably from 100 to 10,000 Pa, and further preferably from 500 to 5,000 Pa. The suction pressure may be measured by mounting a Manostar gauge in a box within a suction conveyer.

A continuous elongated workpiece including the exothermic layer 11 and the water-retention layer 12 is obtained by the above described operations, and the obtained workpiece is cut into pieces having desired sizes to form the heating element 10.

In addition to the above, a means for maintaining non-oxidation atmosphere may be employed as desired in the above-described method, in order to suppress the oxidation of the oxidizable metal during the production process.

Figure 4:
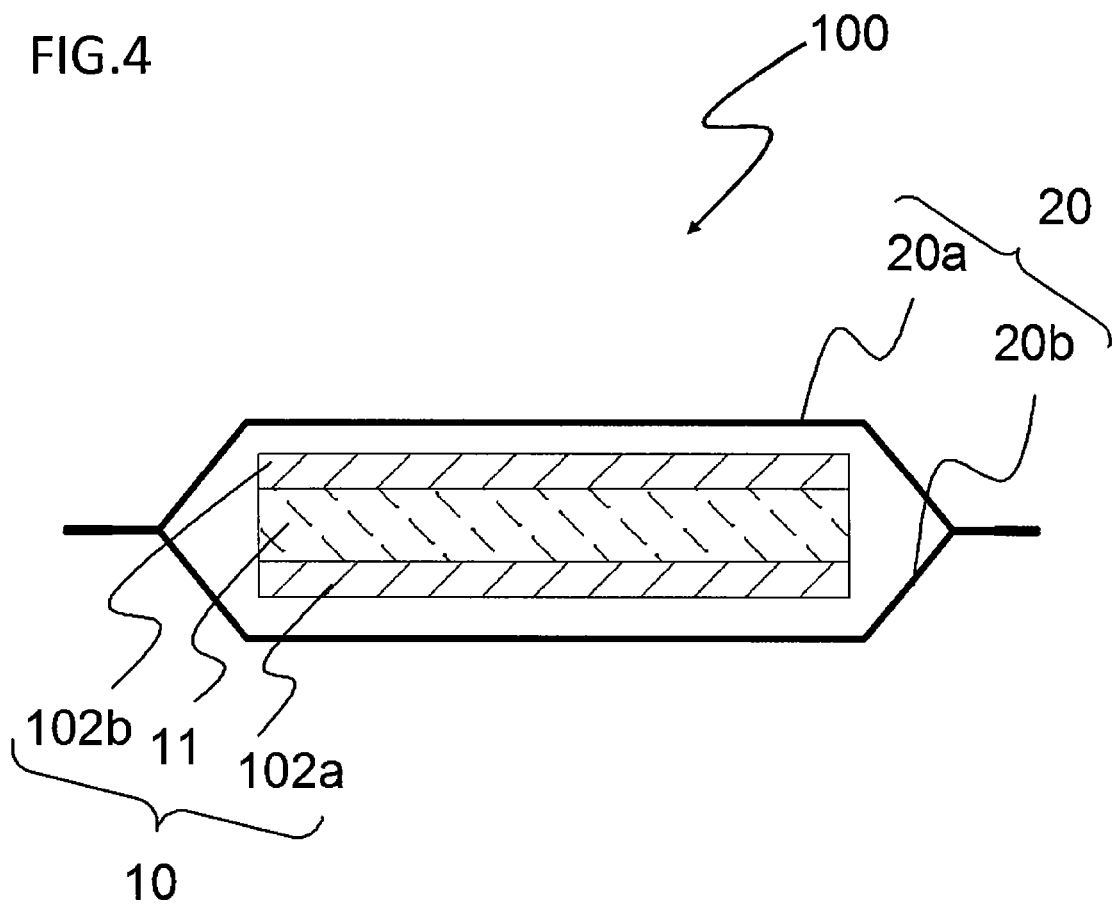
FIG. 4 is a cross-sectional view, which schematically shows a heating implement according to an embodiment.

FIG. 4 is a schematic cross-sectional view, showing an example of the heating implement including the heating element 10 shown in FIG. 2. As shown here, this heating implement 100 includes the heating element 10 having the sandwich structure, in which the exothermic layer 11 is interposed between the first water absorption sheet 102*a* and the second water absorption sheet 102*b*, and a bag 20, which leastwise partially has air permeability and is capable of housing the heating element 10 therein.

More specifically, this heating implement 100 has a configuration, in which the heating element 10 having the exothermic layer 11 and the water-retention layer 12 is put in the bag 20 that leastwise partially has air permeability, and the circumference of the bag 20 is joined to provide a seal. Since the exothermic layer 11 is sandwiched between the water-retention layers 12 in the heating implement 100, unwanted adhesion of the exothermic layer 11 to the bag 20 can be prevented.

The bag 20 is preferably composed of a first bag sheet 20*a* and a second bag sheet 20*b*.

Each of the first bag sheet 20*a* and the second bag sheet 20*b* has a projecting field that projects from the outer circumference of the heating element 10 toward the outside thereof, and it is preferable the respective projecting fields thereof are joined. This joining preferably provides continuous airtightness in the circumference. The bag 20 formed by the joining of the first bag sheet 20*a* with the second bag sheet 20*b* has a space in the interior thereof for containing the heating element therein. The heating element 10 is contained in this space. The heating element 10 may be in the condition of being fixed to the bag 20, or in the condition of being not fixed thereto.

A portion of, or the entirety of the first bag sheet 20*a* has air permeability. Air resistance (JIS P 8117) of the first bag sheet 20a is preferably from 1,000 to 50,000 seconds/100 ml, is more preferably from 2,000 to 35,000 seconds/100 ml, and is more preferably from 5,000 to 20,000 seconds/100 ml.

It is preferable to employ, for example, a porous sheet of a synthetic resin having moisture permeability but having no water permeability for the first bag sheet 20a having such an air resistance. More specifically, a film manufactured by stretching polyethylene containing calcium carbonate may be employed. When such porous sheet is employed, various types of fiber sheets including one, two or more nonwoven fabric(s) selected from needle punch nonwoven fabric, air through nonwoven fabric and spunbond nonwoven fabric may be laminated over the outer surface of the porous sheet to provide an enhanced texture of the first bag sheet 20a. The first bag sheet 20a may be an air permeable sheet, a portion of or the whole of which having air permeability, or may alternatively be a non-air permeable sheet having no air permeability, and may be preferably made of a sheet having a higher air permeability than the second bag sheet 20b (that is, the sheet exhibiting lower air resistance).

In addition to the above, the air resistance (JIS P 8117) of the first bag sheet 20a is preferably equal to or lower than 50,000 seconds/100 ml, is further preferably equal to or lower than 35,000 seconds/100 ml, and preferably equal to or lower than 20,000 seconds/100 ml. On the other hand, the air resistance (JIS P 8117) of the first bag sheet 20a is preferably equal to or higher than 1,000 seconds/100 ml, is further preferably equal to or higher than 2,000 seconds/100 ml, and preferably equal to or higher than 5,000 seconds/100 ml.

The second bag sheet 20b may be an air permeable sheet, a portion of or the whole of which has air permeability, or may alternatively be a non-air permeable sheet having no air permeability, and may be preferably made of a sheet having lower air permeability than the second bag sheet 20a (that is, the sheet exhibiting higher air resistance).

When the second bag sheet 20b is composed of a non-air permeable sheet, a film manufactured with synthetic resin having a single layer or multiple layers may be employed, or various types of fiber sheets including one, two or more nonwoven fabric(s) selected from needle punch nonwoven fabric, air through nonwoven fabric and spunbond nonwoven fabric may be laminated over the outer surface of the aforementioned film manufactured with synthetic resin having a single layer or multiple layers to provide enhanced texture of the second bag sheet 20b. More specifically, a dual-layered film composed of a polyethylene film and a polyethylene terephthalate film, a laminate film composed of a polyethylene film and a nonwoven fabric, a laminate film composed of a polyethylene film and a pulp sheet and the like may be employed, and the laminate film composed of a polyethylene film and a pulp sheet is especially preferable.

When the second bag sheet 20b is an air permeable sheet, the bag sheet that is the same as the first bag sheet 20a may be employed, or a different bag sheet may alternatively be employed. When a different bag sheet is employed, the air resistance of the second bag sheet 20b is preferably from 5,000 to 150,000 seconds/100 ml, and is more preferably from 8,000 to 100,000 seconds/100 ml, as long as the air permeability of the second bag sheet 20b is lower than the air permeability of the first bag sheet 20a.

The air resistance of the second bag sheet 20b (JIS P 8117) is preferably equal to or lower than 150,000 seconds/100 ml, and is further preferably equal to or lower than 100,000 seconds/100 ml. On the other hand, the air resistance of the second bag sheet 20b (JIS P 8117) is preferably equal to or higher than 5,000 seconds/100 ml, and is further preferably equal to or higher than 8,000 seconds/100 ml.

Among these, it is especially preferable when the air resistance of the first bag sheet 20a falls within a range from 5,000 to 20,000 seconds/100 ml and the air resistance of the second bag sheet 20b falls within a range from 15,000 to 80,000 seconds/100 ml. Such air resistance can provide improved oxidation reaction of the oxidizable metal and in addition generate a larger quantity of water vapor from the side of the first bag sheet 20a.

These sheets are preferably arranged so that the first water absorption sheet 102a is disposed on the side of the first bag sheet 20a and the second water absorption sheet 102b is disposed on the side of the second bag sheet 20b, and the circumference sections are tightly sealed to achieve improved oxidation reaction of the oxidizable metal and to achieve improved capability of generating a larger quantity of water vapor from the side of the first bag sheet 20a.

In addition to the above, in the case that the water-retention layer 12 is formed only on one side of the exothermic layer 11, for example, a direct contact of the exothermic layer with the second bag sheet 20b may be possibly caused when only the first water absorption sheet 102a is employed without employing the second water absorption sheet 102b, and therefore it is preferable to employ a non-air permeable sheet for the second bag sheet 20b in such case, in order to avoid the possibility of causing a change in the air permeability of the second bag sheet 20b due to adhesion of the exothermic layer.

A single heating element 10 may be housed in the bag 20, or those in multiple-layered configuration may alternatively be housed therein.

Various types of fiber sheets may be laminated for the bag 20 in order to provide enhanced texture as described above, and further may be contained in an exterior package having air permeability (not shown) to improve the texture and the usability. Such exterior package may preferably be composed of a first exterior sheet and a second exterior sheet, and may be configured so that the first exterior sheet covers one surface of the bag 20 and the second exterior sheet covers the other surface of the bag 20, and the first exterior sheet is joined with the second exterior sheet in the projecting field that projects from the outer circumference of the bag 20 towards the outside thereof, and further it is preferable to join the sheets with a tight seal. This allows forming a space in the interior of the exterior package for containing the bag 20 therein, and the heating element 10 enclosed with the bag 20 can be contained in this space. The bag 20 may be in the condition of being fixed to the exterior package, or may be in a non-fixed condition.

The air permeability of the exterior package sheet or more specifically, of the first exterior sheet and the second exterior sheet is preferably equal to or lower than 3,000 seconds/100 ml and is more preferably from 1 to 100 seconds/100 ml, as long as it is higher than the air permeability of the first bag sheet 20a. Such air resistance can provide improved oxidation reaction of the oxidizable metal and in addition generate a larger quantity of water vapor.

The types of the first and the second exterior sheets composing the exterior package are not limited to any specific type and typically are various types of fiber sheets including nonwoven fabrics and the like, as long as the material has air permeability, and for example, one, two or more selected from a needle punch nonwoven fabric, an air through nonwoven fabric and a spunbond nonwoven fabric may be employed.

The heating implement 100 may serve as a vapor heating implement, which is capable of generating water vapor by the oxidation reaction of the oxidizable metal, provided that the bag 20 has air permeability and the exterior package also has air permeability.

The heating implement 100 may include an adhesive layer (not shown), which is formed by applying an adhesive agent over the outer surface of the exterior package, or for example, over the surface of the first exterior sheet or the second exterior sheet constituting the exterior package. The adhesive layer is utilized for fixing the heating implement 100 on human skin or clothes or the like. Materials, which have been typically employed in the technical field, including a hot melt adhesive agent and the like, may be employed for the adhesive agent constituting the adhesive layer.

It is preferable that the heating implement 100 is stored in a tightly sealed condition in a package bag (not shown) having an oxygen barrier property until just before the use thereof.

The heating implement 100 may be directly applied to a human body, or may be mounted on clothes to be preferably employed for warming the human body. The applicable sites on the human body may include, for example, shoulder, neck, eye, the circumference of the eye, waist, elbow, knee, thigh, leg, abdomen, lower abdomen, hand, sole of foot and the like. This is also applicable to various types of articles other than the human body to be preferably employed for warming or heat retention. Further, if the heating implement 100 is a type of heating implement for creating water vapor, water vapor may also be applied with the warming.

In addition to the above, the above-described heating element 10 may be employed for a heating implement having constitutions other than those shown in FIG. 4 or for other applications.

While the preferred embodiments of the present invention have been described above in reference to the annexed figures, it should be understood that the disclosures above are presented for the purpose of illustrating the present invention, and various modifications other than that described above are also available.

Concerning the embodiment as described above, the present invention will further disclose the following compositions, production methods or applications thereof.

<1> A heating element including: an exothermic layer containing an oxidizable metal, a water absorption agent and water; and a water-retention layer having a water absorption sheet, wherein the exothermic layer and the water-retention layer are in layers, wherein the mass ratio of the content of the water absorption agent is from 0.3 to 20 parts by mass for 100 parts by mass of the oxidizable metal, wherein the mass ratio of the content of water to the content of the water to the content of the water absorption agent in the exothermic layer (water/water absorption agent) is from 0.8 to 13, and wherein the content of water contained in the water-retention layer is from 10 to 45 mass % of the maximum water absorption of the water-retention layer.

<2> The heating element as described in <1>, in which the water absorption agent contains a carbon component, and the content of the carbon component is equal to or higher than 90 mass % for the mass of the water absorption agent.

<3> The heating element as described in <1> or <2>, in which the water absorption agent contains a carbon component, and the mean particle diameter of the carbon component is from 10 to 200 μm.

<4> The heating element as described in any one of <1> to <3>, in which the exothermic layer further contains a thickening agent.

<5> The heating element as described in any one of <1> to <4>, in which the air resistance of the water-retention layer is equal to or lower than 500 seconds/100 ml under a condition that water in the amount of from 10 to 45 mass % of the maximum water absorption is absorbed.

<6> The heating element as described in any one of <1> to <5>, in which the water-retention layer is formed of a first water absorption sheet and a second water absorption sheet, and the exothermic layer is interposed between the first water absorption sheet and the second water absorption sheet.

<7> A heating implement, including: the heating element as described in any one of <1> to <6>; and a bag at least partially having air permeability and is capable of containing the heating element.

<8> The heating implement as described in <7>, in which the implement is capable of creating water vapor as an occurrence of an oxidation of an oxidizable metal.

<9> The heating element as described in any one of <1> to <6>, in which the exothermic layer contains a thickening agent, and the mass ratio of the content of the thickening agent is from 0.05 to 5 parts by mass for 100 parts by mass of the oxidizable metal.

<10> The heating element as described in any one of <1> to <6> or <9>, in which the exothermic layer contains a thickening agent, and the thickening agent contains a polysaccharide-based thickening agent having molecular weight of equal to or higher than 1,000,000 and equal to or lower than 50,000,000.

<11> The heating element as described in any one of <1> to <6> or <9> or <10>, in which the mean particle diameter of the oxidizable metal is from 10 to 200 μm.

<12> The heating element as described in any one of <1> to <6> or in any one of <9> to <11>, in which the content of the oxidizable metal is from 100 to 3,000 g/m$^2$.

<13> The heating element as described in any one of <1> to <6> or in any one of <9> to <12>, in which the content of the water absorption agent is from 3 to 13 parts by mass for 100 parts by mass of the oxidizable metal.

<14> The heating element as described in any one of <1> to <6> or in any one of <9> to <13>, in which the mean particle diameter of the carbon component is from 12 to 100 μm.

<15> The heating element as described in any one of <1> to <6> or in any one of <9> to <14>, in which the content of the water absorption agent is from 4 to 290 g/m$^2$.

<16> The heating element as described in any one of <1> to <6> or in any one of <9> to <15>, in which the content of the carbon component is equal to or higher than 98 mass % for mass of the water absorption agent.

<17> The heating element as described in any one of <1> to <6> or in any one of <9> to <16>, in which the content of the water-absorbing polymer in the water absorption agent is equal to or lower than 10 mass %.

<18> The heating element as described in any one of <1> to <6> or in any one of <9> to <17>, in which the mass ratio (water/water absorption agent) in the exothermic layer is from 1.5 to 10.

<19> The heating element as described in any one of <1> to <6> or in any one of <9> to <18>, in which the content of water contained in the water-retention layer is from 13 to 30 mass % of the maximum water absorption of the water-retention layer.

<20> The heating element as described in any one of <1> to <6> or in any one of <9> to <19>, in which the air resistance of the water-retention layer is from 1 to 300 seconds/100 ml under a condition that water in an amount of from 10 to 45 mass % of the maximum water absorption is absorbed.

<21> The heating element as described in any one of <1> to <6> or in any one of <9> to <20>, in which the water-retention layer contains a fiber material, the fiber length of which is from 0.5 to 6 mm.
<22> The heating element as described in any one of <1> to <6> or in any one of <9> to <21>, in which a thermally bonded fiber is blended in the water-retention layer, and the blending quantity of the thermally bonded fiber is from 0.1 to 10 mass % for the whole quantity of the fibers in the water-retention layer.
<23> The heating element as described in any one of <1> to <6> or in any one of <9> to <22>, in which the water-retention layer contains water-absorbing polymer and particle diameter of the water-absorbing polymer is from 1 to 1,000 μm.
<24> The heating element as described in any one of <1> to <6> or in any one of <9> to <23>, in which the ratio of the water-absorbing polymer to the water-retention layer is from 10 to 70 mass % under the dried condition.
<25> The heating element as described in any one of <1> to <6> or in any one of <9> to <24>, in which grammage of the water-retention layer is from 20 to 200 g/m$^2$ under the dried condition.
<26> The heating element as described in any one of <1> to <6> or in any one of <9> to <25>, in which the heating element further contains a reaction accelerator agent, and the content of the reaction accelerator agent is from 2 to 15 parts by mass for 100 parts by mass of the oxidizable metal.
<27> A heating implement, including: the heating element as described in any one of <1> to <6> or in any one of <9> to <26>; and a bag being capable of containing the heating element, in which the bag is composed of a first bag sheet and a second bag sheet, air resistance of the first bag sheet is from 1,000 to 50,000 seconds/100 ml, air resistance of the second bag sheet is the same as, or different from the air resistance of the first bag sheet, and in the case the air resistance is different therefrom, it is from 5,000 to 150,000 seconds/100 ml, as long as it is lower than the air permeability of the first bag sheet.
<28> The heating implement as described in <27>, in which the bag is further contained on an exterior package having air permeability.
<29> The heating implement as described in <28>, in which the exterior package is composed of a first exterior sheet and a second exterior sheet, and air permeability thereof is equal to or lower than 3,000 seconds/100 ml, as long as it is higher than the air permeability of the first bag sheet 20*a*.
<30> The heating implement as described in <28> or <29>, further including an adhesive layer in an outer surface of the exterior package.

EXAMPLES

Examples 1 and 2 and Comparative Example 3

Heating implements, each having a structure as shown in FIG. 4, were produced as follows.
[Preparation of Composition of Exothermic Powder Dispersed in Water]
An oxidizable metal, a water absorption agent, water, a reaction accelerator agent and a thickening agent were prepared according to the relative proportions of the components as shown in Table 1, and the productions were carried out by the following procedures. The thickening agent was dissolved in water, and then the reaction accelerator agent was dissolved therein to prepare an aqueous solution. Meanwhile, a powder mixture made by pre-mixing an oxidizable metal and a water absorption agent was prepared, and such pre-mixed powder was added to the aqueous solution, and then the mixture was stirred with disc turbine stirring blades at 150 rpm for 10 minutes to obtain an composition of exothermic powder dispersed in water in the form of a slurry.

Here, information on product types, product names and/or manufacturers for the oxidizable metal, the water absorption agent, water, the reaction accelerator agent, and the thickening agent are as follows.
Oxidizable metal: iron powder: (iron powder RKH, commercially available from DOWA IP CREATION Co., Ltd.), mean particle diameter 45 μm;
Water absorption agent: activated carbon (CARBORAFFIN, commercially available from Japan EnviroChemicals, Ltd.) mean particle diameter 40 μm;
Water: tap water
Reaction accelerator agent: sodium chloride (Japanese Pharmacopoeia sodium chloride, commercially available from Otsuka Chemical Co., Ltd.); and
Thickening agent: Xanthan gum, (Echogum BT commercially available from DSP GOKYO FOOD & CHEMICAL Co., Ltd.), molecular weight 2,000,000
[Preparation of Heating Element]
A polymer sheet is manufactured by stacking: a paper made of wood pulp (grammage 20 g/m$^2$, commercially available from Inokami Co., Ltd.);
a water-absorbing polymer (spherical, mean particle diameter 300 μm, AQUALIC CA, commercially available from Nippon Shokubai Co., Ltd., grammage 30 g/m$^2$); and
another paper made of wood pulp (grammage 30 g/m$^2$, commercially available from Inokami Co., Ltd.)
and combining them into a single sheet to be employed as a first water absorption sheet
(air resistance in the condition that water in the amount of from 10 to 45 mass % of the maximum water absorption is absorbed: 2 seconds/100 ml), and
a paper made of wood pulp (grammage 50 g/m$^2$, commercially available from Inokami Co., Ltd.) was employed as a second water absorption sheet. The polymer sheet to be employed as the first water absorption sheet was prepared, and the composition of exothermic powder dispersed in water, which had been prepared according to the above descriptions, was applied over a surface of the first water absorption sheet of 25 cm$^2$ (5 cm×5 cm) to form a thickness of substantially 3 mm, and then the applied surface was covered with the second water absorption sheet of 25 cm$^2$ (5 cm×5 cm) to obtain a heating element I and a heating element II, each having a different content of the exothermic composition as show in Table 1.
[Preparation of Heating Implement]
Each of the heating elements of Examples 1 and 2 and Comparative Example 3 was put in a bag having air permeability (6.5 cm×6.5 cm: air resistance of a first bag sheet 5,000 seconds/100 ml, air resistance of a second bag sheet 20,000 seconds/100 ml), so that the first water absorption sheet is disposed on the side of the first bag sheet and the second water absorption sheet is disposed on the side of the second bag sheet, and then the circumference section was tightly sealed. Further, a peripheral section of a surface of an exterior bag (7.5 cm×7.5 cm) made of an air through nonwoven fabric (air resistance 1 second/100 ml, 30 g/m$^2$) was coated with an adhesive agent with an area of 1 cm wide×4 cm long at 100 g/m$^2$, and was further covered with a release paper, and the bag containing the heating element was put in the exterior bag and then the circumference section thereof was tightly sealed to obtain a heating implement. The heating implement was stored in an oxygen insulation bag until an evaluation, as will be discussed later, was started. Here, in Table 1, a heating implement obtained by employing the heating element I was represented as a heating implement I, and a heating implement obtained by employing the heating element II was represented as a heating implement II. Further, a series of operations were conducted under a nitrogen gas-stream atmosphere.

Comparative Example 1, 2

Heating implements were produced similarly as in Examples 1 and 2, except that an exothermic powder prepared as shown below was employed as the heating element.
[Preparation of Exothermic Powder]
According to the relative proportions of the components as shown in Table 1, an oxidizable metal, a water absorption agent, water and a reaction accelerator agent were mixed to prepare an exothermic composition. More specifically, a saline solution was added to a powder mixture made by pre-mixing iron powder and activated carbon, and the mixture was stirred for 10 minutes to prepare an exothermic composition. Here, a series of operations were conducted under a nitrogen gas-stream atmosphere.

Comparative Example 4

A heating implement was produced similarly as in Examples 1 and 2, except that a paper-produced heating element produced as follows was employed as the heating element.
[Preparation of Paper-Produced Heating Element]
Oxidizable metal: iron powder (commercially available from DOWA IP CREATION Co., Ltd., trade name "RKH"), 83 mass %;
Wood pulp: pulp fiber (NBKP, manufacturer: Fletcher Challenge Canada Ltd., trade name "Mackenzi," CSF 200 ml), 8 mass %; and
Water absorption agent: activated carbon (mean particle diameter 40 μm, CARBORAFFIN, commercially available from Japan EnviroChemicals, Ltd.), 9 mass %.
For 100 parts by mass of the above-described raw compositions: 0.2 parts by weight of coagulant: sodium carboxymethylcellulose (commercially available from Dai-ichi Kogyo Seiyaku Co., Ltd., trade name "CELLOGEN WS-C") and 0.3 parts by mass of polyamide epichlorohydrin resin (commercially available from JAPAN PMC Corporation, trade name "WS552").
Water: industrial water was added until the solid content concentration thereof reached to 0.3 mass %.
<Paper-Making Conditions>
The above-described raw compositions were employed to carry out paper-making with a gradient-type "tanmo" paper machine to manufacture a formed sheet in wet condition.
<Drying Condition>
The sheet was pinched with a felt, and was pressurized to be dehydrated, and then was introduced between heating rollers of 120 degrees C. to carry out drying until the water content was equal to or lower than 5 mass %. Then, a paper-produced sheet (exothermic intermediate sheet) having grammage of 450 g/m² and thickness of 0.25 mm was obtained.
<Condition for Adding Electrolytic Solution>
42 parts by mass of an electrolytic solution was added to 100 parts by mass of the exothermic intermediate sheet by coating the dried paper-produced sheet (exothermic intermediate sheet) with the following electrolytic solution to obtain a produced-paper heating element.
<Electrolytic Solution>
electrolyte: refined salt (NaCl)
water: industrial water
electrolytic solution concentration: 5 mass %
[Evaluation]
The following evaluations were made on the heating elements of Examples 1 and 2 and Comparative Examples 1 to 4, and the heating implement including the heating elements. The evaluation results were shown in Table 1.
1. Measurement of Water Content
Water percentage and water content of the exothermic layer, water content of the water-retention layer, and the maximum water absorption of the water-retention layer of the heating elements of Examples 1 and 2 and Comparative Example 3 were determined as follows.
<1> Water Percentage ($R_{H2O}$) and Water Content ($W_{11}$) of Exothermic Layer
2 g of the exothermic layer, which had been formed on the water-retention layer, was collected, and a moisture tester (Kett moisture tester, FD-240, commercially available from Kett Electric Laboratory Co., Ltd.) was employed to determine the water percentage $R_{H2O}$ of the exothermic layer by measuring the quantity of the exhausted water during the thermal drying at 120 degrees C. for 15 minutes. The water content of the exothermic layer was calculated with the following formula (2).

water percentage of exothermic layer ($R_{H2O}$)=quantity of exhausted water/sample quantity (i.e., 2 g)  (formula 1)

water content in exothermic layer ($W_{11}$)=content of exothermic composition×solid content percentage of exothermic composition (total of relative proportions of components except water/total of relative proportions of components)×measured water percentage $R_{H2O}$/(1−measured water percentage $R_{H2O}$)  (formula 2)

<2> Water Content of Water-Retention Layer ($W_{12}$)
The water content of the water-retention layer was calculated with the following formula (3).

water content of water-retention layer ($W_{12}$)=content of exothermic composition×water percentage of exothermic composition (relative proportion of water/total of relative proportions of components)−(<1>(water content of exothermic layer)  (formula 3)

<3> Maximum Water Absorption of Water-Retention Layer ($W_{max}$)
The maximum water absorption of the water-retention layer ($W_{max}$) was measured according to the measuring method of JIS L 1906 as follows. A first water absorption sheet before being coated with composition of exothermic powder dispersed in water [paper made of wood pulp (grammage 20 g/m², commercially available from Inokami Co., Ltd.)/water-absorbing polymer (AQUALIC CA, commercially available from Nippon Shokubai Co., Ltd., grammage 30 g/m²)/paper made of wood pulp (grammage 30 g/m², commercially available from Inokami Co., Ltd.), thickness 0.5 mm] and a second water absorption sheet (paper made of wood pulp (grammage 50 g/m²)) were cut into a dimension of 25 cm² to measure the mass ($W_0$) of the cut piece, and then, the cut piece was dipped in 5 mass % sodium chloride aqueous solution for five minutes. The piece was then taken out with tweezers, and was maintained as being hung in the air for one minute during which water that could not be retained in the piece drips, and then the mass of the piece was measured and the maximum water absorption ($W_{max}$) was calculated according to the following formula.

$$W_{max} = W_1 - W_0$$

The result was that the maximum water absorption ($W_{max}$) of the water-retention layer (first water absorption sheet+second water absorption sheet) in Example was 2.62 g/25 cm².

2. Measurement of Heat Generation

Measurements of heat generation were conducted with a measurement device based upon JIS S 4100 by sticking the surface of the heating implement on the side of the first bag sheet on the measurement surface of the measurement device. More specifically, the evaluation was made using the maximum temperature (degrees C.).

Figure 5:
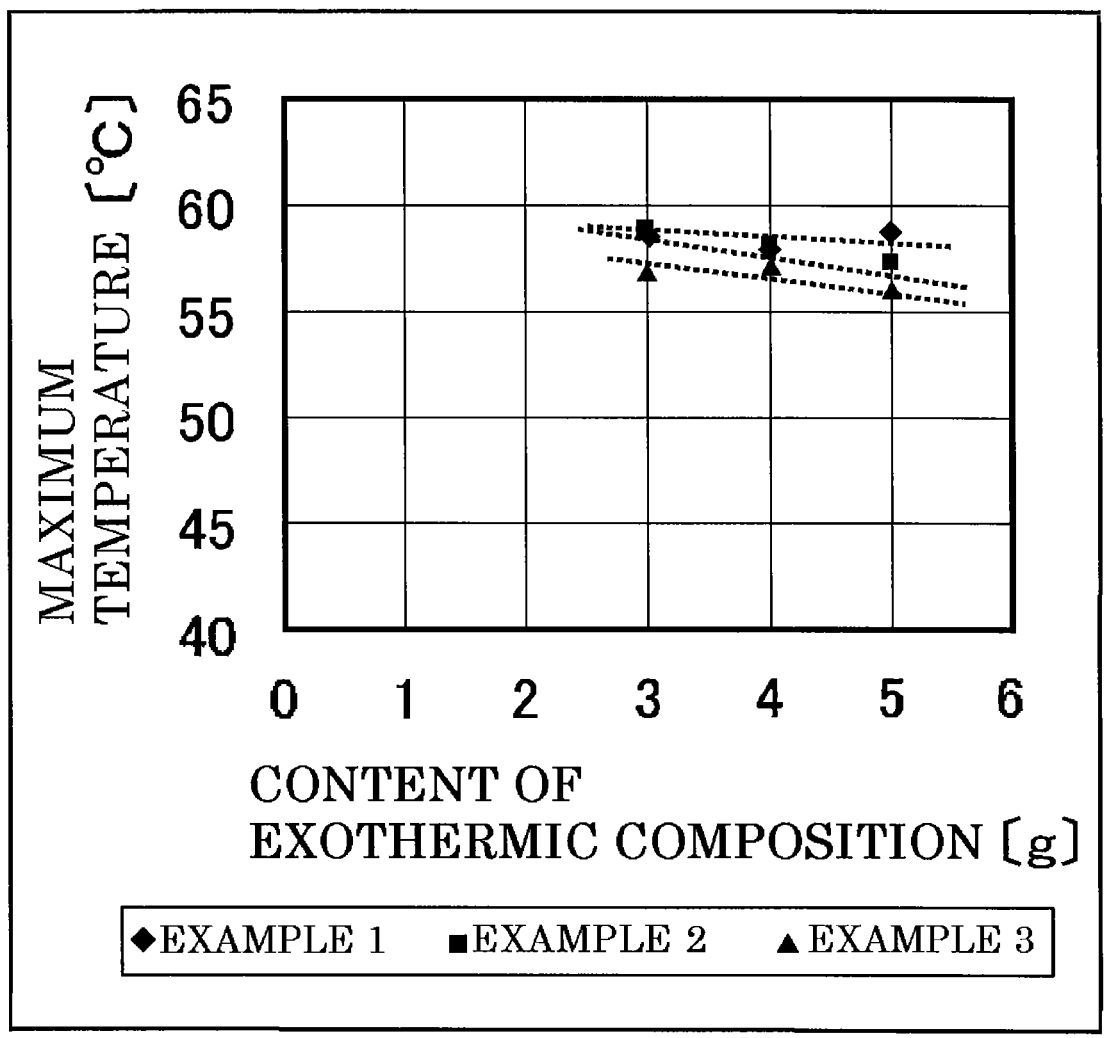
FIG. 5 is a graph, which shows evaluation results in Examples.

FIG. 5 shows relations of the maximum temperature (degrees C.) with the content of the heat generation composition in the heating element for the heating implements of Examples 1 and 2. FIG. 6 shows relations of the maximum temperature (degrees C.) with the content of the heat generation composition in the heating element for the heating implements of Comparative Examples 1, 2 and 4. FIG. 6(a) represents evaluation results of the heating implement of Comparative Examples 1 and 2, and FIG. 6(b) represents evaluation results of the heating implement of Comparative Example 4. No considerable change in the maximum temperature was caused in the heating implements of Examples 1 and 2 even when the content of the heat generation

TABLE 1

| | | Example 1 | Example 2 | Comparative Example 1 | Comparative Example 2 | Comparative Example 3 | Comparative Example 4 |
|---|---|---|---|---|---|---|---|
| EXOTHERMIC COMPOSITION (PARTS BY MASS) | IRON POWDER (MEAN DIAMETER 45 μm) | 100 | 100 | 100 | 100 | 100 | 100 |
| | ACTIVATED CARBON (MEAN DIAMETER 40 μm) | 8 | 12 | 4 | 12 | 4 | 10.8 |
| | WOOD PULP | | | | | | 9.6 |
| | WATER | 62 | 72 | 32 | 34 | 38 | 49.2 |
| | SODIUM CHLORIDE | 3.5 | 3.5 | 3.5 | 3.5 | 3.5 | 2.6 |
| | XANTHAN GUM (MEAN MOLECULAR WEIGHT 2,000,000) | 0.2 | 0.2 | | | 0.2 | |
| | TOTAL AMOUNT | 173.7 | 187.7 | 139.5 | 149.5 | 145.7 | 172.2 |
| HEATING ELEMENT I | CONTENT OF EXOTHERMIC COMPOSITION I (g) | 3.0 | 3.0 | 3.0 | 3.0 | 3.0 | 3.0 |
| | GRAMMAGE OF IRON POWDER IN EXOTHERMIC COMPOSITION (g/m') | 691 | 639 | 860 | 803 | 824 | 697 |
| | EXOTHERMIC LAYER | WATER CONTENT $W_{11}$/WATER ABSORPTION AGENT (MASS RATIO) | 3.3 | 1.6 | 8.0 | 2.8 | 6.6 | 2.4 |
| | WATER-RETENTION LAYER | WATER CONTENT IN WATER-RETENTION LAYER/MAXIMUM WATER ABSORPTION $W_{12}/W_{max}$ | 21.8% | 31.1% | — | — | 7.6% | — |
| HEATING IMPLEMENT I | MAXIMUM TEMPERATURE (° C.) | 58.3 | 58.9 | 58.5 | 57.0 | 59.0 | 58.0 |
| HEATING ELEMENT II | CONTENT OF EXOTHERMIC COMPOSITION II (g) | 4.0 | 4.0 | 4.0 | 4.0 | 4.0 | 4.63 |
| | GRAMMAGE OF IRON POWDER IN EXOTHERMIC COMPOSITION (g/m') | 921 | 852 | 1.147 | 1.070 | 1.098 | 1.075 |
| | EXOTHERMIC LAYER | EXOTHERMIC LAYER $W_{11}$/WATER ABSORPTION AGENT (MASS RATIO) | 3.8 | 2.2 | 8.0 | 2.8 | 7.0 | 2.4 |
| | WATER-RETENTION LAYER | WATER CONTENT IN WATER-RETENTION LAYER/MAXIMUM WATER ABSORPTION $W_{12}/W_{max}$ | 25.9% | 36.4% | — | — | 8.6% | — |
| HEATING IMPLEMENT II | MAXIMUM TEMPERATURE (° C.) | 58.1 | 58.0 | 60.9 | 59.6 | 60.4 | 60.8 |
| HEATING IMPLEMENT | DIFFERENCE IN MAXIMUM TEMPERATURES (HEATING IMPLEMENT II – HEATING IMPLEMENT I) | −0.2 | −0.9 | 2.4 | 2.6 | 1.4 | 2.8 |

The maximum temperature was substantially constantly maintained in each of the heating elements of Examples 1 and 2, regardless of the difference in the content of the heat generation composition to provide better heat generation characteristics, and on the contrary, unusual heat generation (increase in the maximum temperature) was found in each of the heating element of Comparative Examples 1 to 4, in response to increase in the content of the heat generation composition (I (3 g) to II (4 g)).

Since excessive heat generation hardly occurs in the heating elements of Examples 1 and 2, regardless of the variations in the content of the heat generation composition, in particular the quantity of the oxidizable metal, these heating elements are considered to be the heating elements exhibiting enhanced production stability.

On the contrary, in the heating elements of Comparative Examples 1 to 4, excessive temperature elevation was found composition in the heating element was changed, and on the contrary, in the case of the heating implements of Comparative Examples 1, 2 and 4, the maximum temperature was increased as the content of the heat generation composition in the heating element was increased.

The invention claimed is:

1. A heating element, comprising:
   (a) an exothermic layer containing an oxidizable metal, a water absorption agent and water; and
   (b) a water-retention layer having a first water absorption sheet and a second water absorption sheet, and said exothermic layer is interposed between said first water absorption sheet and said second water absorption sheet,
   wherein said exothermic layer and said water-retention layer are in layers, wherein a first mass ratio of the content of said water absorption agent is from 0.3 to 20 parts by mass for 100 parts by mass of the oxidizable metal, wherein a second mass ratio of the content of water to the content of said water absorption agent in said exothermic layer (water/water absorption agent) is from 0.8 to 13, and wherein the content of water in said water-retention layer is from 10 to 45 mass % of the maximum water absorption of said water-retention layer.

2. The heating element according to claim 1, wherein said water absorption agent comprises at least one member selected from the group consisting of a carbon component, a fiber material, a water-absorbing polymer, and a water-absorbing powder.

3. The heating element according to claim 1, wherein said water absorption agent comprises a carbon component, and the content of said carbon component is equal to or higher than 90 mass % for the mass of said water absorption agent.

4. The heating element according to claim 1, wherein said water absorption agent comprises a carbon component, and wherein the mean particle diameter of said carbon component is from 10 to 200 μm.

5. The heating element according to claim 1, wherein said exothermic layer further comprises a thickening agent.

6. The heating element according to claim 1, wherein said water-retention layer comprises a fiber material.

7. The heating element according to claim 1, wherein said water-retention layer comprises a water-absorbing polymer which is capable of absorbing and maintaining a significant amount of liquid that is 20 times its own weight.

8. The heating element according to claim 7, wherein the ratio of said water-absorbing polymer to said water-retention layer is from 10 to 70 mass % under the dried condition.

9. The heating element according to claim 1, wherein the grammage of said water-retention layer is from 20 to 200 g/m$^2$ under the dried condition.

10. The heating element according to claim 1, wherein air resistance of said water-retention layer is equal to or lower than 500 seconds/100 ml under a condition that an amount of water from 10 to 45 mass % of the maximum water absorption is absorbed.

11. The heating element according to claim 1, wherein said exothermic layer comprises a thickening agent, and the content of said thickening agent is from 0.05 to 5 parts by mass for 100 parts by mass of the oxidizable metal.

12. The heating element according to claim 1, wherein said exothermic layer comprises a thickening agent, and said thickening agent comprises a polysaccharide-based thickening agent having the molecular weight of equal to or higher than 1,000,000 and equal to or lower than 50,000,000.

13. A heating implement, comprising:

the heating element according to claim 1; and a bag which is at least partially air permeable and capable of containing said heating element.

14. The heating implement according to claim 13, wherein said bag is composed of a first bag sheet and a second bag sheet, and the air resistance of said first bag sheet is from 1,000 to 50,000 seconds/100 ml.

15. The heating implement according to claim 14, wherein the air resistance of said second bag sheet is from 5,000 to 150,000 seconds/100 ml, as long as the air permeability of said second bag sheet is lower than the air permeability of said first bag sheet.

16. The heating implement according to claim 13, wherein the implement is capable of creating water vapor as an occurrence of an oxidation of an oxidizable metal.

\* \* \* \* \*